United States Patent
Krause et al.

(10) Patent No.: US 7,108,849 B2
(45) Date of Patent: Sep. 19, 2006

(54) HAIR WAX PRODUCT WITH REDUCED DENSITY

(75) Inventors: Thomas Krause, Darmstadt (DE); Bernd Stein, Hoesbach (DE); Axel Kalbfleisch, Darmstadt (DE); Werner Brocks, Burghaun (DE); Michael Franzke, Rossdorf (DE); Thomas Schulz, Darmstadt (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 11/028,365

(22) Filed: Jan. 3, 2005

(65) Prior Publication Data

US 2005/0118127 A1    Jun. 2, 2005

(51) Int. Cl.
*A61Q 5/06* (2006.01)

(52) U.S. Cl. ..................... 424/70.2; 424/70.1

(58) Field of Classification Search ............... None
See application file for complete search history.

(56) References Cited

U.S. PATENT DOCUMENTS 6,139,849 A * 10/2000 Lesaulnier et al. ......... 424/401

* cited by examiner

*Primary Examiner*—Jyothsna Venkat
(74) *Attorney, Agent, or Firm*—Michael J. Striker

(57) ABSTRACT

The wax composition for styling human hair provides hold, strength and rigidity, includes at least one wax and/or waxy material, and has a density of less than or equal to 0.9 g/ml, after being foamed in a fluid or softened state with a gas, preferably air or a non-reactive gas, such as nitrogen, so that it includes a bubble and/or pore structure. In the method for styling human hair this wax composition is applied to the hair and the hair is shaped with the wax composition applied to it.

16 Claims, No Drawings

HAIR WAX PRODUCT WITH REDUCED DENSITY

BACKGROUND OF THE INVENTION

The subject matter of the invention is a solid hair wax product, which contains at least one solid wax or a solid wax-like or waxy material and whose density is reduced to less than or equal to 0.9 g/ml by introduction of gases.

Hair waxes have been used for hair styling for a long time. They can be used to shape the hairstyle with the help of the fingers. They are especially useful in imparting hold, rigidity and strength, as well as luster, to the hairstyle and for putting short to medium length hair in a fashionable arrangement. Also hair waxes produce texture and shape in the hairstyle. Commercial hair waxes are usually provided in cups or dishes. The procedure for using them is based on the following principles: A mass of the product is removed with the fingers. The wax is distributed on the surface of the hand, whereby it is melted or greatly softened by the heat in the hand. Because of that softening or melting the otherwise solid wax can be worked into the hair. The wax is worked into the hair in a softened or more or less liquid state. In the hair it is cooled and again achieves its original consistency. It is hardened and provides stability and hold to the resulting hairstyle. Frequently it provides a wet-look. Because of these operation principles these waxes and the obtained product performance of the commercial wax styling products are considerably limited. So that the wax is easily removed from the dish or cup, easily applied and sufficiently worked into the hair, its melting or softening point must be in the vicinity of the body temperature and it must not be too hard when it is taken from the hand. The maximum melting or softening temperature of commercial wax products is thus limited to at maximum about 40° C. On the other hand, only a limited product performance in regard to stability of the hairstyle, hold and volume of the hairstyle, can be obtained with this sort of comparatively soft wax product. Besides that the load on the hair provided by these known products is comparatively high. Of course an improved fixing and improved hold with reduced amounts and reduced loads can be obtained with a hardened, higher melting wax composition. However the harder, the wax, the harder and more difficult it is to remove it from the cup or dish and work it into the hair.

SUMMARY OF THE INVENTION

It is an object of the present invention to provide hair waxes, which provide improved styling with reduced load on the hair and, at the same time, satisfactory application properties in regard to workability and surface texture, i.e. roughness or smoothness, in contrast to conventional hair wax products.

An additional disadvantage of commercial pan wax products is that the wax mass usually must be removed during application with the fingers from the pan, which can lead to contamination of the rest of the product in the pan. An additional object of the present invention is to find a way to avoid contamination of the remaining product mass in the vessel in which it is marketed or provided.

It was surprisingly found that the basic purity requirements for a wax product are attained when a wax mass comprising a hardened high melting wax is foamed with gas. Hard wax material is more easily removed from the product by rubbing, i.e. by applying a mechanical load by hand to the wax mass, when the wax mass is foamed to introduce partially observable gas bubbles or pores. This is true even if the temperature of the hand of the user is significantly under the characteristic softening temperature of the wax mass. This is probably due to two different physical effects: First less heat is required to soften the wax mass on its surface in order to slide a portion of wax film off the boundary surface between the wax product and the hand, because of the reduced density and larger specific surface area of the foamed wax mass. By sliding a film off the surface by rubbing and shearing, the user can more easily soften a portion of the wax mass with his hand. Since the wax cannot be melted by heat of the hand alone, the missing energy can be furnished by shearing a wax portion from the wax mass. The wax mass is such that there is already a comparatively large energy increase with a comparatively small shear load, as is clearly indicated from the temperature behavior. Already the wax mass is heated up several degrees Centigrade by a small increase in shear.

After application to the hair and the cooling and solidification connected with the application, these hard waxes provide even greater possibilities for hairstyling and hair shaping, since they permit a stiff bundling of hair. This aspect is of great importance for a fashion-trend-oriented styling product.

Improved storage stability at higher temperatures is an additional advantage of the product according to the invention. The heat transport to the interior of the wax mass is prevented by the bubble structure, since the foam has an insulating effect. This behavior is advantageous, in the event that there is an unsuitably high storage temperature, since it prevents the melting of the entire wax mass and the loss of gas bubbles.

It is also possible to provide the wax product according to the invention in a completely different alternative administration form than conventional wax products filled in pans or dishes, which is an additional advantage. It is possible to shape the hair wax product into three dimensional bodies, blocks, rods, tablets, which have advantageous predetermined openings. It is possible for the user to proportion the wax in a hygienically unobjectionable manner and to break off a sufficient amount from the tablet or the rod for use. The advantage of this sort of administration is a reduction in contamination, which cannot be excluded when the wax material is removed by the fingers from conventional wax products.

The clearly improved cosmetic appeal and appearance of the wax mass is another advantage to the foaming. The accompanying use of high melting waxes, especially natural waxes, such as beeswax, usually produces a yellowish brown color in the formulation, which frequently is not desired. The color of the product is greatly lightened by foaming with the gas bubbles and the product appears clearly whiter, brighter and pleasanter.

The methods, which are adapted for foaming the wax mass described here, are already employed in the food industry for foaming of semisolid and creamy milk products, such as yogurt or cottage cheese and fat containing products, such as chocolate (see G. B. Patent 459,583, U.S. Pat. No. 5,238,698). Thus the introduced gas can form a discontinuous phase or a continuous phase (see e.g. U.S. Pat. No. 4,889,738). These known methods are chiefly also suitable for manufacture of the hair wax products according to the invention.

The subject matter of the invention thus is a solid (at room temperature, i.e. 20° C.) hair wax product comprising or containing at least one wax ingredient selected from the group consisting of waxes and waxy materials. The term "solid wax product" means a product that is solid at 20° C. This product has durability or stability after storage for at least one week at 20° C. and a density of less than or equal to 0.9 g/ml, preferably of 0.4 to 0.8 g/ml. The solid hair wax products according to the invention are made by introducing a gas into the at least one wax ingredient, the waxes and/or waxy materials, when the at least one wax ingredient is in liquid form or in a softened state, which is sufficiently soft for foaming. The hair wax products according to the invention are employed to provide hold, strength and/or rigidity to a human hairdo or hairstyle.

In the agents according to the invention the wax mass is foamed with air or a non-reactive gas in a sufficient amount so that the density of the finished product is less than or equal to 0.9 g/ml, especially 0.2 to 0.8 g/ml, especially preferably from 0.4 to 0.7 g/ml. Besides air the gas used for foaming can be a non-reactive gas, e.g. nitrogen, carbon dioxide, nitrogen oxides, noble gases or mixture of these gases. Compressed air is preferred because of economical reasons. When oxidation sensitive ingredients are employed the use of non-reactive, oxygen-free gases, such a nitrogen or carbon dioxide, is preferred.

The hair wax products according to the invention are characterized by a largely homogeneous distribution of pores or gas bubbles in a solid wax matrix. The pore and/or bubble structure and the reduced density connected with them are stable, i.e. they are constant for a time interval of at least one week, preferably at least one month, especially preferably at least six months during storage at room temperature (20° C.). The pores and bubbles typically have a size of between 0.0001 and 5 mm, preferably from 0.01 to 1 mm, especially preferably from 0.1 to 0.8 mm.

Wax Materials

In the following the term "wax" is used for any suitable wax and waxy material. "Wax" is the technical term for a series of natural, partially synthetic or synthetic materials, which have common physical and application properties. The term "wax" relates particularly to the definition of wax in Ullmanns' Encyclopedia of Industrial Chemistry, 4th Edition, Volume 24, p. 3. According to that definition waxes at 20° C. are kneadable or plastic, solid to brittle, coarse to finely crystalline, transparent to opaque, but not glassy, melting over 40° C. (melting or liquefying point) without decomposition with a comparatively low viscosity already slightly above its melting point (e.g. melt viscosity <10000 mPa s at 10° C. above the liquefying point), strongly temperature dependent in its consistency and solubility and polishable under gentle pressure.

The hair wax product according to the invention, prior to foaming, has a needle penetration number of preferably greater than or equal to 10, especially greater than or equal to 20 (measurement unit 0.1 mm, sample weight 100 g, test duration 5 s, test temperature 25° C., according to DIN 51 579). The waxes are preferably contained in the wax product in an amount of 5 to 80 percent by weight, especially preferably from 20 to 60 percent by weight, and most preferably from 30 to 50 percent by weight. They have a needle penetration number in an unfoamed or not-foamed state, which is less than that of the finished foamed product.

Waxes that can be used are chiefly the known waxes of the prior art. These include natural waxes, (e.g. insect, animal and plant waxes), fossil waxes (e.g. crude oil wax, lignite coal wax, peat wax or ozocerite), mineral waxes, synthetic waxes (e.g. Fischer-Tropsch waxes, polyolefin waxes, such as polyethylene or polybutene wax, amide waxes) and partially synthetic waxes, microcrystalline waxes, macrocrystalline waxes, hydrocarbon waxes, especially solid high-melting paraffin waxes, petrolatum, Vaseline®, montan wax, acid-functionalized hydrocarbon waxes (e.g. obtained by oxidation of hydrocarbon materials, such as polyolefins or paraffin or by copolymerization of ethylene with acid-containing comonomers, such as acrylic acid or vinyl acetates), beeswax, wool wax and their derivatives, such as wool wax alcohol, candelilla wax, carnauba wax, Japan wax, hard fats, fatty acids and fatty alcohols with e.g. 10 to 22 carbon atoms, fatty acid esters, fatty alcohol esters, fatty acid glycerides and monoesters or diesters of the formula $R^1$—(C=O)$OR^2$, $R^1$—(C=O)$OR^3$—O(C=O)$R^1$ and $R^2$O(C=O)—$R^3$—(C=O)$OR^2$, wherein $R^1$ stands for a $C_8$- to $C_{22}$-alkyl group, $R^2$ for a $C_3$- to $C_{22}$-alkyl group and $R^3$ for a $C_2$ to $C_{16}$-alkylene group, as well as polyglycol waxes and silicone waxes. These waxes have a solidification point about room temperature (20° C.), preferably above 40° C., especially preferably above 55° C. The needle penetration number (units, 0.1 mm, 100 g, 5 s, at 25° C.; according to DIN 51 579) is from 2 to 70, especially from 3 to 40. Preferably the waxes contain at least one wax which has a needle penetration number of less than 40, especially preferably less than 20. Carnauba wax and ceresin or their mixtures with a needle penetration number of less than 20 are preferred.

Because of improved washability polyglycol waxes, especially waxy polyethylene glycols, polyglycol monomethyl ethers and propylene oxide-ethylene oxide copolymers, are preferred waxes. Polyethylene glycols (PEG) are especially preferred. Suitable PEGs include soft waxes (800 to 2000 g/mol) or hard waxes (r>2000 g/mol), whose melting points range up to a maximum of about 60° C., depending on their molecular weight. The high molecular weight PEGs are waxy solids at room temperature (20 to 25° C.). For products according to the invention the molecular weight amounts to particularly 2500 to 6000 g/mol, preferably from 2700 to 5000 g/mol. Polyethylene glycols have the general formula $H(OCH_2CH_2)_nOH$. Suitable high molecular weight polyethylene glycols include those with n=57 to 113, preferably with n=61 to. 79. Suitable polyethylene glycols have an INCI number PEG-60 (n=60), PEG-75 (n=75), PEG-90 (n=90) and PEG-100 (n=100). PEG-60 and PEG-70 are especially preferred. Commercial products usually have a molecular weight distribution. Suitable commercial products are e.g. polyglycol 3000 with a molecular weight of 2700 to 3000 or polyglycol 4000 of Clariant with a molecular weight of 3700 to 4500. The polyglycol 4000 is more preferable than the polyglycol 3000, since it imparts improved rigidity to the hair. Also soft waxy PEGs are contained having a molecular weight of 800 to 2000 g/mol.

Additional Hydrophobic Oils

To additionally improve the wax products according to the invention hydrophobic fats or oils can be included in them. The non-volatile oils are especially preferred. The amounts of these hydrophobic fats or oils used can be up to five percent by weight, preferably from 0.1 to 4 percent by weight. Non-volatile, hydrophobic oils have a melting point under 25° C. and a boiling point of over 250° C., preferably over 300° C. All oils of this type known to one skilled in the art can be used in the wax products according to the invention. Suitable hydrophobic fats or oils include plant or animal oils, mineral oils, silicone oils or their mixtures. Suitable silicone oils include polydimethylsiloxanes, phenylated silicones, polyphenylmethylsiloxanes, phenyltrimethicones, poly($C_1$–$C_{20}$)-alkylsiloxanes and alkylmethylsiloxanes. Furthermore hydrocarbon oils, for example paraffin oils, isoparaffin oils, squalene, oils from fatty acids and polyols, especially triglycerides, are suitable. Suitable vegetable oils include, e.g., sunflower seed oil, coconut oil, castor oils, lanolin oil, jojoba oil, corn oil and soy oil. Hydrocarbon oils, especially mineral oils (*paraffinum liquidum*) and liquid alkanes with 14 or more carbon atoms, are especially preferred.

Additional Emulsifiers

In preferred embodiments the wax products according to the invention also include at least one emulsifier in order to improve the washability of the composition from the hair. The emulsifiers are, preferably, present in an amount of from 0.1 to 25 percent by weight, especially from 0.5 to 20 percent by weight, particularly preferably from 3 to 15 percent by weight. Preferred emulsifiers are selected from the classes of non-ionic surfactants. For example the following nonionic surfactants are suitable:

- addition products of 2 to 30 mol ethylene oxide and/or 1 to 5 mol propylene oxide at $C_8$- to $C_{22}$-fatty alcohols, to $C_{12}$- to $C_{22}$-fatty acids or to alkyl phenols with 8 to 15 carbon atoms in the alkyl groups,
- $C_{12}$- to $C_{22}$-fatty acid monoesters and diesters of addition products of 1 to 30 mol ethylene oxide in glycerol,
- addition products of 5 to 60 mol ethylene oxide in castor oil or to hardened (hydrogenated) castor oil, and
- monoesters, diesters and/or triesters of phosphoric acids with addition products of 2 to 30 mol ethylene oxide to $C_8$- to $C_{22}$-fatty alcohols.

In an especially preferred embodiment the emulsifiers themselves similarly have a waxy consistency and a drop point over 25° C.

Other Ingredients

The wax products of the invention can also contain additional ingredients besides the above mentioned ingredients including the following:

- solvents, such as water or univalent or multivalent $C_1$- to $C_4$-alcohols, especially ethanol, propanol, glycerol or glycols in an amount of up to 10 percent by weight, preferably from 0.1 to 8 percent by weight;
- cosmetic dye compounds in an amount up to six percent by weight, preferably from 0.1 to 4 percent by weight, e.g. C.I.Pigment Red 4 (C.I. 12 085), C.I. Pigment Green (C.I. 74 260), and/or C.I. Vat Blue 4 (C.I. 69 800);
- pearlescent pigments in an amount of up to 25 percent by weight, preferably from 1 to 20 percent by weight, e.g. those on a titanium dioxide/mica basis;
- perfume and fragrance in an amount of up to 2 percent by weight, preferably 0.01 to 1 percent by weight;
- preservatives in an amount of up to 1 percent by weight, especially preferably from 0.01 to 0.5 percent by weight, especially parahydroxybenzoic acid ester, benzoic acid, salicylic acid, sorbic acid, mandelic acid, polyhexa-methylenebiguanide hydrochloride or isothazolinone derivatives, for which the sorbic acid derivative has proven to be especially suitable;
- film-forming polymers, such as polyvinyl pyrrolidone or vinyl-pyrrolidone/vinyl acetate copolymers, in an amount of up to five percent by weight, preferably from 0.1 to four percent by weight; and
- hair care additives, such as betaine, in an amount of up to five percent by weight, preferably from 0.01 to 4 percent by weight.

Manufacturing Methods

The agent according to the invention can be made, when (1) a solid wax composition containing a wax and/or a waxy material is provided;

(2) this wax composition is converted by energy transfer, for example heating and/or application of shear energy, to a liquid form or to a softened state, sufficiently soft for foaming with a gas; and (3) air and/or a non-reactive gas, such as nitrogen, is introduced into this liquid or softened composition in an amount such that the density of the finished wax product of the invention is less than or equal to 0.9 g/ml.

Preferably the wax composition is first melted at a temperature, which is clearly above its melting and/or drop point and which is higher than the temperature, at which the subsequent foaming occurs. The melted wax is tempered with shearing in a stirring device. The wax mass remains fluid and can be stirred by energy transfer due to the shearing, when the temperature is under the solidification point. The foaming with continuous shearing occurs at temperatures, which typically are between 10° C. above the solidification point and preferably up to 40° C. under the solidification point of the wax mass. The gas is introduced into the liquid or softened wax mass. For this purpose the gas is supplied by application of a low pressure (vacuum) to a stirred vessel or by means of an overpressure in a gas tube or pipe. The overpressure for supply of the gas amounts to e.g. 1.2 to 8 bar, preferably 2 to 5 bar. Pressurized air is preferably used. By changing the feed rate, rotation speed, temperature, pressure and amount of gas supplied the density, the consistency and foam bubble size may be adjusted as desired. The gas quantity introduced is selected so that the density for the finished product is at maximum 0.9 g/ml, preferably from 0.2 to 0.8 g/ml, especially preferably from 0.4 to 0.7 g/ml. The average bubble and/or pore size amount to from 0.1 to 0.2 mm.

When the gas is supplied with a low pressure, a gas bubble and pore structure is built up in the wax mass in which the gas has been introduced because of the pressure difference between the pressure in the mixing apparatus and the atmospheric pressure during filling. Cooling stabilizes the bubble structure and the wax mass is solidified in connection with that. The same effect can be achieved, when the gas is introduced into the fluid wax mass under normal pressure. By application of a low pressure the gas bubbles introduced into the wax mass expand. The bubble structure is stabilized by cooling.

The stable foamed wax products ideally are in a still fluid or extrudable state in a suitable package, such as in a cup or pan or in a suitably shaped portion. The wax products can be formed as a three-dimensional molded body and for example are in the shape of a block, rod or tablet. They can have break-away portions, preferably in the form of chocolate tablets, for example formed by break-away indentations or notches in a wax body. This permits the user to break away portions sufficient for application without contamination of the remaining portions.

Application

The products are applied, when an amount of the product sufficient for application is removed from the package and/or broken off from the three-dimensional body with the break-away portions. Sufficient energy is supplied by shearing and hand heat so that the wax mass is sufficiently softened so that a portion of it can be removed from the wax mass by rubbing and worked into the hair. After solidifying in the hair the wax crystallizes, solidifies and imparts an outstanding rigidity to the hair.

EXAMPLES

Example 1

Foamed Hair Wax Based on Hydrophobic Waxes

A wax mass was prepared with the following ingredients:

| | |
|---|---|
| 46.4 g | paraffinum perliquidum |
| 25.0 g | ceresin |
| 10.0 g | carnauba wax |
| 10.0 g | triceteareth-4 phosphate |
| 5.0 g | beeswax |
| 3.0 g | ethoxylated and hydrogenated castor oil, ethoxylated with 25 ethylene oxide units |
| 0.4 g | perfume |
| 0.2 g | propyl parabene |

The wax mass was melted at about 60° C. and fed by means of a pump through a Kratz-Schabe cooler. The wax mass was then tempered to about 30 to 40° C. The mass was then fed to the mixing head of a dynamic foam generator Top Mix (Hansa Industry Mixer) at a feed speed of 15 to 20 l/h. Nitrogen was supplied with an overpressure of 1.5 to 5 bar and mixed with the mass in the mixing head at 200 to 300 revolutions per minute. It was cooled externally in order to compensate for a temperature increase caused by shear energy. The mass was fed from the mixer through a valve at a temperature of about 30° C. with a buttery consistency. The gas bubble introduced into the mass expanded because of the reduction in the external pressure to standard pressure. After complete cooling the wax mass solidified and had a density of 0.6 to 0.8 g/ml.

The foamed product is dispensed from its container by rubbing and worked into the hair considerably easier than the not-foamed wax mass, i.e. the wax mass of the prior art that did not have bubbles introduced into it.

Example 2

Foamed Hair Wax Based on a PEG Waxes

A wax mass was prepared with the following ingredients:

| | |
|---|---|
| 27.6 g | PEG-4 |
| 23.3 g | glycerol |
| 21.0 g | PEG-90 |
| 20.0 g | PEG-60 |
| 3.8 g | water |
| 3.0 g | ethoxylated and hydrogenated castor oil, ethoxylated with 25 ethylene oxide units |
| 1.0 g | paraffinum perliquidum |
| 0.3 g | perfume |

The foamed wax product of example 2 is made by the method of example 1. The foamed product is dispensed from its container by rubbing and worked into the hair considerably easier than the not-foamed wax mass.

The disclosure in German Patent Application 101 28 468.3 of Jun. 12, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in hair wax products with reduced density, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of styling human hair to provide hold, strength and rigidity, said method comprising applying a wax product to the human hair and shaping the human hair with the wax product applied thereto into a hairstyle, wherein said wax product has a density of less than or equal to 0.9 g/ml, said wax product comprises gas bubbles and at least one wax member, said at least one wax member is selected from the group consisting of waxes and waxy materials, said gas bubbles consist of at least one gas, and said at least one gas is selected from the group consisting of air, nitrogen, carbon dioxide, nitrogen oxides, and noble gases.

2. A method of styling human hair to provide hold, strength and rigidity, said method comprising applying a wax product having a density of less than or equal to 0.9 g/ml to the human hair and shaping the human hair with the wax product applied thereto into a hairstyle, wherein said wax product is made by a process comprising the steps of:
  a) providing a solid wax composition containing at least one wax member selected from the group consisting of waxes and waxy materials;
  b) converting said solid wax composition by energy transfer to a liquid form, or to a softened state, sufficiently soft for foaming with a gas; and then
  c) introducing said gas into said wax composition in said liquid form or said softened state in an amount sufficient, so as to form said wax product with said density of less than or equal to 0.9 g/ml.

3. The method as defined in claim 2, wherein said solid wax composition is converted to said melted state during said converting and said converting of said solid wax composition to said melted state comprises melting.

4. The method as defined in claim 2, wherein said solid wax composition is converted to said melted state during said converting and said converting of said solid wax composition to said melted state consists of melting said solid wax composition at a temperature above a melting point of said solid wax composition to form a melted wax composition and then tempering said melted wax composition with shearing in a stirring device so that said melted wax composition remains fluid during said introducing of said gas.

5. The method as defined in claim 2, wherein said introducing consists of foaming said wax composition in said melted state or said softened state with said gas and then cooling to form a stable bubble structure in said wax product.

6. The method as defined in claim 2, wherein said density of said wax product is from 0.4 to 0.8 g/ml.

7. The method as defined in claim 2, wherein said gas is selected from the group consisting of air, nitrogen, carbon dioxide, nitrogen oxides and noble gases.

8. The method as defined in claim 2, wherein said solid wax composition comprises at least one hydrophobic oil.

9. The method as defined in claim 2, wherein said solid wax composition comprises up to 10 percent by weight of at least one solvent selected from the group consisting of water, univalent $C_1$- to $C_4$-alcohols and polyvalent $C_1$- to $C_4$-alcohols, from 0.1 to 25 percent by weight of a non-ionic surfactant, up to 1 percent by weight of a perfume and/or fragrance and up to 1 percent by weight of a preservative.

10. The method as defined in claim 1, wherein said density of said wax product is from 0.4 to 0.8 g/ml.

11. The method as defined in claim 1, wherein said gas bubbles have an average size of from 0.1 to 0.2 mm.

12. The method as defined in claim 1, wherein said wax product comprises at least one hydrophobic oil.

13. The method as defined in claim 1, wherein said wax product comprises from 0.1 to 4 percent by weight of at least one hydrocarbon oil.

14. The method as defined in claim 1, wherein said wax product does not contain water.

15. The method as defined in claim 1, wherein said wax product comprises up to 10 percent by weight of at least one solvent selected from the group consisting of water, univalent $C_1$- to $C_4$-alcohols and polyvalent $C_1$- to $C_4$-alcohols and from 0.1 to 25 percent by weight of a non-ionic surfactant.

16. The method as defined in claim 14 or 15, wherein said wax product comprises up to 1 percent by weight of a perfume and/or fragrance, up to 5 percent by weight of a hair care additive, up to 20 percent by weight of a pearlescent pigment, up to four percent by weight of a film-forming polymer and up to 1 percent by weight of a preservative.

* * * * *

UNITED STATES PATENT AND TRADEMARK OFFICE
CERTIFICATE OF CORRECTION

| | | |
|---|---|---|
| PATENT NO. | : 7,108,849 B2 | Page 1 of 1 |
| APPLICATION NO. | : 11/028365 | |
| DATED | : September 19, 2006 | |
| INVENTOR(S) | : T. Krause et al. | |

It is certified that error appears in the above-identified patent and that said Letters Patent is hereby corrected as shown below:

On the Title page at Col. 1, item (21) Add --This Application is a DIV of Ser. No. 10/170,091 filed June 12, 2002--

Signed and Sealed this

Seventh Day of October, 2008

JON W. DUDAS
*Director of the United States Patent and Trademark Office*